(12) United States Patent  
Tanaka et al.

(10) Patent No.: US 11,986,270 B2  
(45) Date of Patent: May 21, 2024

(54) ULTRASOUND IMAGING APPARATUS THAT ALTERNATES BETWEEN MONITORING AND IMAGING MODES, SURGICAL OPERATION SUPPORT SYSTEM, AND METHOD USING THE SAME

(71) Applicant: Hitachi, Ltd., Tokyo (JP)

(72) Inventors: Tomohiko Tanaka, Tokyo (JP); Teiichiro Ikeda, Tokyo (JP); Ryo Imai, Tokyo (JP); Hirozumi Takeshima, Tokyo (JP)

(73) Assignee: FUJIFILM HEALTHCARE CORPORATION, Chiba (JP)

( * ) Notice: Subject to any disclaimer, the term of this patent is extended or adjusted under 35 U.S.C. 154(b) by 11 days.

(21) Appl. No.: 17/215,187

(22) Filed: Mar. 29, 2021

(65) Prior Publication Data

US 2021/0369121 A1 Dec. 2, 2021

(30) Foreign Application Priority Data

May 28, 2020 (JP) .................................. 2020-093575

(51) Int. Cl.
*A61B 5/00* (2006.01)
*A61B 90/00* (2016.01)
(Continued)

(52) U.S. Cl.
CPC ............ *A61B 5/0095* (2013.01); *A61B 90/37* (2016.02); *A61B 90/50* (2016.02); *A61N 7/00* (2013.01);
(Continued)

(58) Field of Classification Search
CPC ....... A61B 5/0095; A61B 90/37; A61B 90/50; A61B 2090/378; A61N 7/00; A61N 2007/0043; B06B 1/06
See application file for complete search history.

(56) References Cited

U.S. PATENT DOCUMENTS 6,261,232 B1 * 7/2001 Yokosawa ................ A61B 8/00
600/443
9,149,252 B2 * 10/2015 Tashiro ................ A61B 8/5253
(Continued)

FOREIGN PATENT DOCUMENTS

JP 2015139465 A 8/2015
JP 2017-503548 A 2/2017
(Continued)

OTHER PUBLICATIONS

Chinese Office Action received in corresponding Chinese Application No. 202110283843.7 dated Jul. 6, 2023.
(Continued)

*Primary Examiner* — Serkan Akar
*Assistant Examiner* — Gabriel Victor Popescu
(74) *Attorney, Agent, or Firm* — MATTINGLY & MALUR, PC (57) ABSTRACT

Provided are an ultrasound imaging apparatus and a surgical operation support system for obtaining position information of a device outside an imaging area and presenting the position information to a user together with an ultrasound image. The surgical operation support system includes the ultrasound imaging apparatus, an ultrasonic source fixed to a therapeutic tool to be inserted into a subject body, a display device for displaying the ultrasound image and the position of the ultrasonic source. The ultrasound imaging apparatus is provided with a position estimator for estimating the position information of the ultrasonic source, and the position estimator analyzes a grating lobe artifact (false image) that is generated by the ultrasonic wave emitted from the ultrasonic source outside the imaging area, to estimate the position information of the ultrasonic source with respect to the imaging area.

9 Claims, 11 Drawing Sheets

(51) Int. Cl.
*A61B 90/50* (2016.01)
*A61N 7/00* (2006.01)
*B06B 1/06* (2006.01)

(52) U.S. Cl.
CPC .......... *B06B 1/06* (2013.01); *A61B 2090/378* (2016.02); *A61N 2007/0043* (2013.01)

(56) References Cited

U.S. PATENT DOCUMENTS

| | | |
|---|---|---|
| 10,349,917 B2 * | 7/2019 | Boctor .................. A61B 8/461 |
| 10,492,693 B2 * | 12/2019 | Irisawa ................ A61B 8/0841 |
| 2005/0033165 A1 * | 2/2005 | Ustuner ............... A61B 8/5269 |
| | | 600/443 |
| 2016/0350620 A1 * | 12/2016 | Rao ...................... A61B 8/5269 |
| 2018/0229053 A1 * | 8/2018 | Krueker ........... A61B 2034/206 |
| 2021/0321977 A1 * | 10/2021 | Megens ........... A61B 2090/378 |

FOREIGN PATENT DOCUMENTS

| | | |
|---|---|---|
| JP | 2017-148407 A | 8/2017 |
| JP | 2019-134958 A | 8/2019 |
| JP | 2019-532711 A | 11/2019 |
| JP | 2019-213680 A | 12/2019 |
| JP | 2019-536574 A | 12/2019 |

OTHER PUBLICATIONS

Japanese Office Action received in corresponding Japanese Application No. 2020-093575 dated Dec. 26, 2023.

\* cited by examiner

ULTRASOUND IMAGING APPARATUS THAT ALTERNATES BETWEEN MONITORING AND IMAGING MODES, SURGICAL OPERATION SUPPORT SYSTEM, AND METHOD USING THE SAME

INCORPORATION BY REFERENCE

The present application claims priority from Japanese patent application JP-2020-093575 filed on May 28, 2020, the content of which is hereby incorporated by reference into this application.

BACKGROUND OF THE INVENTION

Field of the Invention

The present invention relates to a surgical operation support technique that combines a photoacoustic technique and an ultrasound imaging apparatus. More particularly, the present invention relates to a technique for monitoring movement of a surgical instrument, when the surgical instrument such as a catheter is inserted into a patient's body and moved to an operation target site.

Description of the Related Art

In a surgical operation for treating blood vessel stenosis, catheter treatment is widely adopted, which is less patient burden than a thoracotomy operation. Visibility is a problem in conducting operation in extremely small areas such as the catheter treatment. A small-diameter device, such as a guidewire, is visible mainly with the use of fluoroscopy, but the positional relationship between an affected area of a living body and the device is indistinct. Particularly in the intravenous treatment, knowing the positional relationship between a vessel wall and the guidewire is directly linked to an operation result, and high visibility is important. There are some attempts to solve this problem by using an ultrasound imaging apparatus during the operation, but it is not easy to delineate the guidewire tip using ultrasonic waves. Therefore, a skilled sonographer is required in addition to the operator, and thus this method has not been adopted widely so far.

On the other hand, there is suggested a technique where an ultrasonic transmitter is attached to the tip of the catheter, and the ultrasound imaging apparatus receives ultrasonic waves from this ultrasonic transmitter to obtain an image, thereby detecting the tip of the catheter. For example, in the technique disclosed by JP-A-2015-139465 (hereinafter, referred to as Patent Document 1), based on a posture detected by a posture detection means attached to the ultrasound probe, the state of the ultrasonic transmitter directly below the ultrasound probe is ensured and the position of the ultrasonic transmitter is detected.

Those techniques that combine the photoacoustic technique with the ultrasound imaging apparatus to grasp the device position, as disclosed by Patent Document 1 and other similar documents, intend to visualize the device tip equipped with the photoacoustic means, when the device is included in the imaging area. Therefore, until the device enters the imaging area, it is not possible to know from which direction the device is approaching and how close it is. In other words, until the device gets near the affected area, it is not possible to predict at all where the device will appear on the ultrasound image of the affected area. In addition, generally, there are many branches in vessels, and when catheter treatment is performed, the device has to proceed, passing through these branches, to reach the predetermined affected area. However, in the conventional methods, even if the traveling direction of the device is deviated, it cannot be detected from the image.

The present invention aims to provide an ultrasound imaging apparatus being able to obtain position information of the device that is outside the imaging area, and to present the position information to a user together with the ultrasound image.

SUMMARY OF THE INVENTION

In order to solve the problems above, an ultrasound imaging apparatus of the present invention utilizes a grating lobe artifact (false image) caused by an ultrasonic wave from outside the imaging area, thereby identifying position information of an ultrasonic source attached to a device, when the ultrasonic source is outside the imaging area.

The ultrasound imaging apparatus of the present invention includes, a transmitter configured to transmit to a subject, an ultrasonic signal being beamformed through an ultrasound probe, a receiver configured to beamform and receive a reflected ultrasonic wave from an imaging area irradiated with the ultrasonic signal, an image former configured to create an ultrasound image of the imaging area, from the reflected ultrasonic wave received by the receiver, and a position estimator configured to use an ultrasonic wave emitted from an ultrasonic source inserted into the subject, the ultrasonic wave being received during a time when the ultrasonic signal is not transmitted from the transmitter, to estimate position information of the ultrasonic source, wherein the position estimator analyzes a false image generated by the ultrasonic wave emitted from the ultrasonic source outside the imaging area, to estimate the position information of the ultrasonic source with respect to the imaging area.

A surgical operation support system of the present invention includes the ultrasound imaging apparatus having the above-described configuration, an ultrasonic source fixed to a therapeutic tool to be inserted into a subject, and a display device configured to display the ultrasound image and a position of the ultrasonic source.

A surgical operation support method of the present invention is a method that uses an ultrasound imaging apparatus for monitoring a surgical instrument inserted into a patient's body, comprising, transmitting and receiving ultrasonic signals repeatedly to and from a predetermined imaging area, forming and displaying an ultrasound image, generating an ultrasonic wave from an ultrasonic source fixed to the surgical instrument during an interval of transmitting and receiving the ultrasonic signals, creating an image from the ultrasonic signals received by the ultrasound imaging apparatus, analyzing a false image of the ultrasonic source outside the imaging area, and estimating and presenting position information of the ultrasonic source with respect to the imaging area.

In the ultrasound imaging apparatus that performs imaging, setting a predetermined region as an imaging area, i.e., under a beamforming condition where phasing is performed within the predetermined region, ultrasonic waves emitted from the outside of the imaging area are made to an image as a false image. This false image is similar to grating lobe (hereinafter, referred to as GL) artifacts, and appearance of the GL artifacts varies in accordance with the positional relationship with respect to the imaging area. In the present invention, the GL artifacts are analyzed, and thereby estimating the relationship between the imaging area and the ultrasonic source being the source of the GL artifacts, in particular, an arrival direction of the ultrasonic source toward the imaging area can be estimated. By presenting this arrival direction together with the ultrasound image which is an image of the imaging area, the user is made aware of whether the ultrasonic source surely travels toward the imaging area being shown as an image, and from which direction the ultrasonic source moves toward the target site, allowing the user to predict the traveling of the ultrasonic source.

DETAILED DESCRIPTION OF THE PREFERRED EMBODIMENTS

Figure 1:
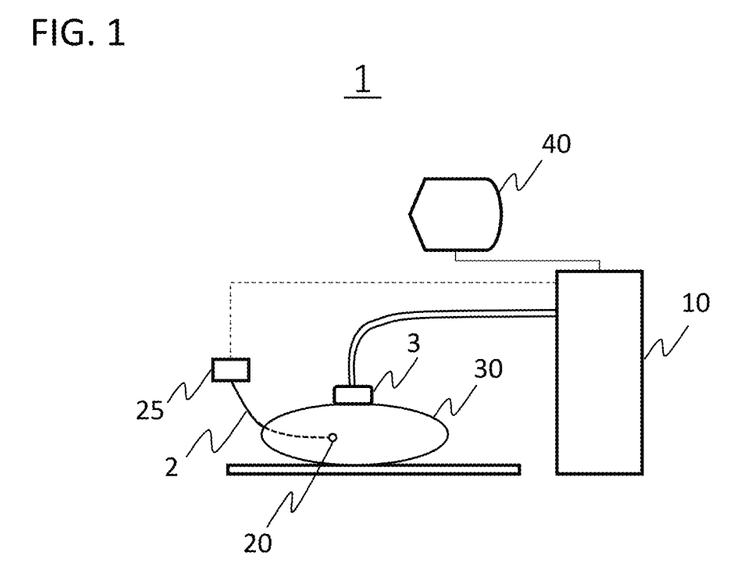
FIG. 1 illustrates an outline of a surgical operation support system according to an embodiment.

There will now be described embodiments of an ultrasound imaging apparatus of the present invention and a surgical operation support system including the same. As shown in FIG. 1, the surgical operation support system 1 includes an ultrasound imaging apparatus 10 to which an ultrasound probe 3 is connected, an ultrasonic source 20 fixed to a device 2, and a display device for displaying an image and others formed by the ultrasound imaging apparatus 10. In the present specification, surgical instruments inserted into a body, such as a therapeutic tool like a balloon catheter or a microcatheter, and a guidewire for carrying the therapeutic tool to a target site, are generically referred to as devices.

The surgical operation support system 1 provides support so that the device 2 can reach an affected portion such as a constricted portion without fail, in a catheter treatment. In the catheter treatment, for example, there is performed a treatment such as expansion of a blood vessel constriction portion, removal of a blood clot and others, after the device 2 is inserted into the body (in the blood vessel) of a subject (patient) 30 to reach the affected portion. Therefore, ultrasonic waves are generated at regular intervals from the ultrasonic source 20 fixed to the device 2, and the ultrasound imaging apparatus 10 detects the ultrasonic waves to estimate the position of the ultrasonic source 20. The ultrasound imaging apparatus 10 transmits ultrasonic waves to the subject 30 and receives reflected ultrasonic waves therefrom, during the time when the ultrasonic waves are not emitted from the ultrasonic source 20, and acquires an ultrasound image of the inside of the subject.

The ultrasonic source 20 comprises an element that generates ultrasonic waves when provided with energy such as light or electricity. Specifically, a piezoelectric element that vibrates at high-frequency signals and emits ultrasonic waves, or a photoacoustic material such as a dye that emits ultrasonic waves upon receipt of light, may serve as this element. The ultrasonic source 20 is connected to a unit for driving the ultrasonic source, the ultrasonic source 20 being connected to a portion of the device 2 inserted into a body. When the ultrasonic source is made of the photoacoustic material, it is connected to a light generator 25 via an optical fiber. In the case of employing the piezoelectric element, a dedicated power source may be used. Alternatively, the piezoelectric element may be connected to the transmitter of the ultrasound imaging apparatus 10, and a signal from the transmitter may drive the piezoelectric element.

Figure 3:
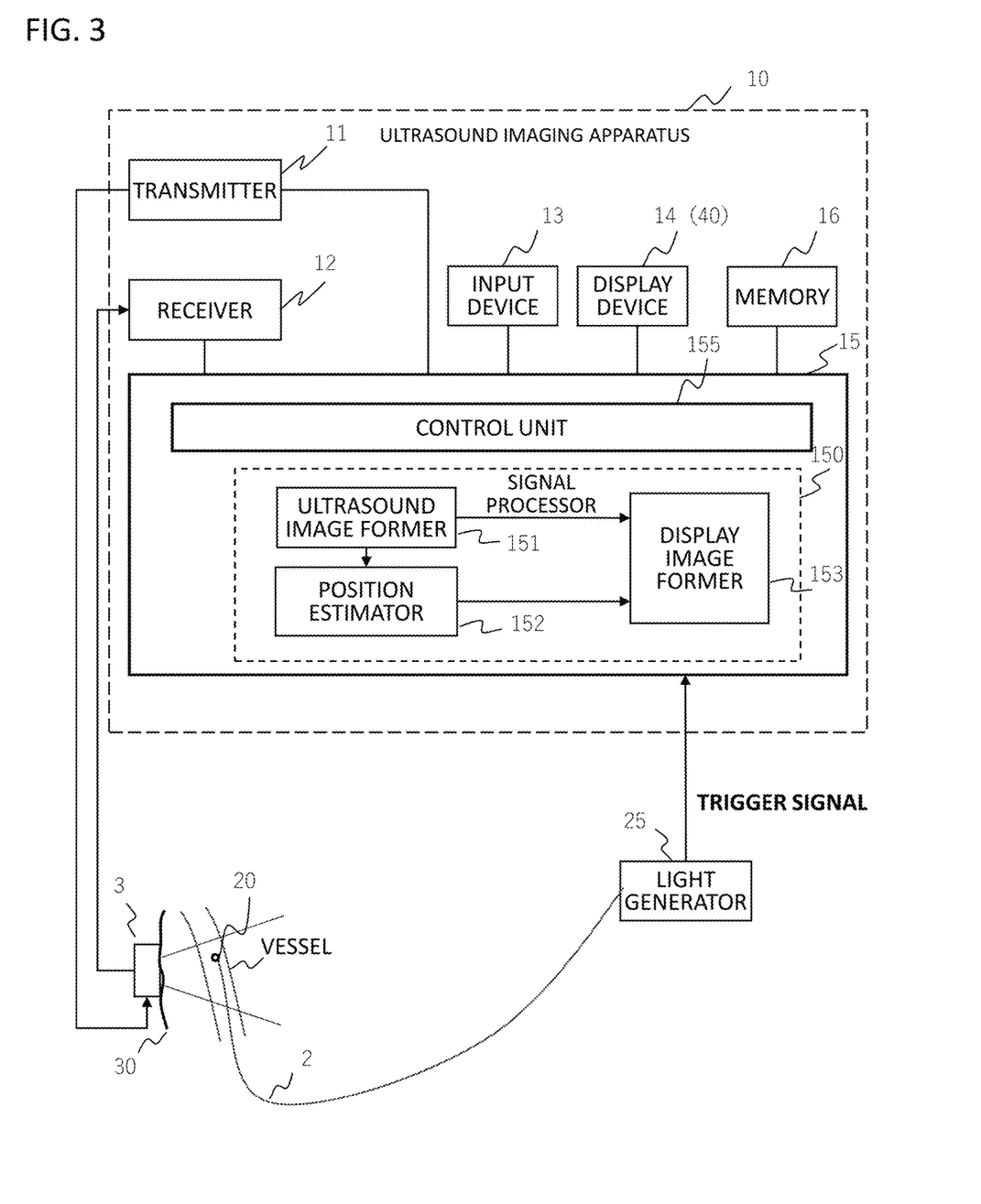
FIG. 3 illustrates an overall configuration of an ultrasound imaging apparatus of Embodiment 1.

As the ultrasound imaging apparatus 10, one having the same structure as a conventional ultrasound imaging apparatus may be used, except that it is provided with a signal processing system including a means for estimating a position of the ultrasonic source 20 (FIG. 3: Position estimator 152). However, a part or all of the functions of the position estimator may be implemented by a signal processor or a computer, separated from the ultrasound imaging apparatus 10. In this case, the ultrasound imaging apparatus 10 shall be provided with an interface unit for exchanging data with the signal processor or the computer. Publicly known means may be employed for the data exchange, such as wired communication, wireless communication, communication via a network and a medium.

An ultrasound image of the inside of the subject is obtained by transmitting ultrasonic beams, beamforming and receiving reflected ultrasonic waves reflected at places inside the subject, and an imaging area is determined by beamforming of the ultrasonic beam and an irradiation angle thereof. On the other hand, the ultrasonic wave emitted from the ultrasonic source 20 spreads in a wave shape and reaches an ultrasound probe, irrespective of the imaging area. When beamforming upon receiving is performed in accordance with the beamforming upon transmitting, an image of the shape of the ultrasonic source 20 is obtained from the ultrasonic waves emitted therefrom, if the ultrasonic source 20 is present within the imaging area. If the ultrasonic source 20 has the shape of dot, a dotted image is obtained. Conventionally, the positional relationship between the affected portion and the device in the real space is identified based on the position of the image of the ultrasonic source 20 in the imaging area. However, when the ultrasonic source 20 is outside the imaging area, the ultrasonic waves therefrom are not rendered as an image of the shape of the ultrasonic source 20 even when the ultrasonic waves therefrom reach the receiver.

In ultrasonic imaging, there is known a phenomenon referred to as grating lobe artifact. A grating lobe (GL) is a pseudo-component that diffuses to the sides of the central axis with respect to original ultrasonic beams, and an image created by the reflected waves from this grating lobe represents the GL artifacts. The GL artifacts occur on the precondition that there exists a grating lobe. However, even spontaneously generated ultrasonic waves, not the reflected waves, may appear as an image, if the condition for generating the grating lobe is satisfied. The condition under which the grating lobe is generated is determined by the arrangement interval d of vibration elements constituting the ultrasound probe, and a wavelength $\lambda$. That is, there is a certain relationship of $\sin\theta = n d/\lambda$ where n is 1, 2, . . . , and $\theta$ indicates the direction of the grating lobe. A false image that appears at this time is generated in the same principle as the grating lobe, and thus it is referred to as GL artifacts here in the present specification.

How the GL artifacts appear from the spontaneous ultrasonic waves varies depending on the position of the ultrasonic source. In the ultrasound imaging apparatus 10 of the present embodiment, the position estimator 152 analyzes the GL artifacts, thereby estimating the position of the ultrasonic source being outside the imaging area.

Figure 2:
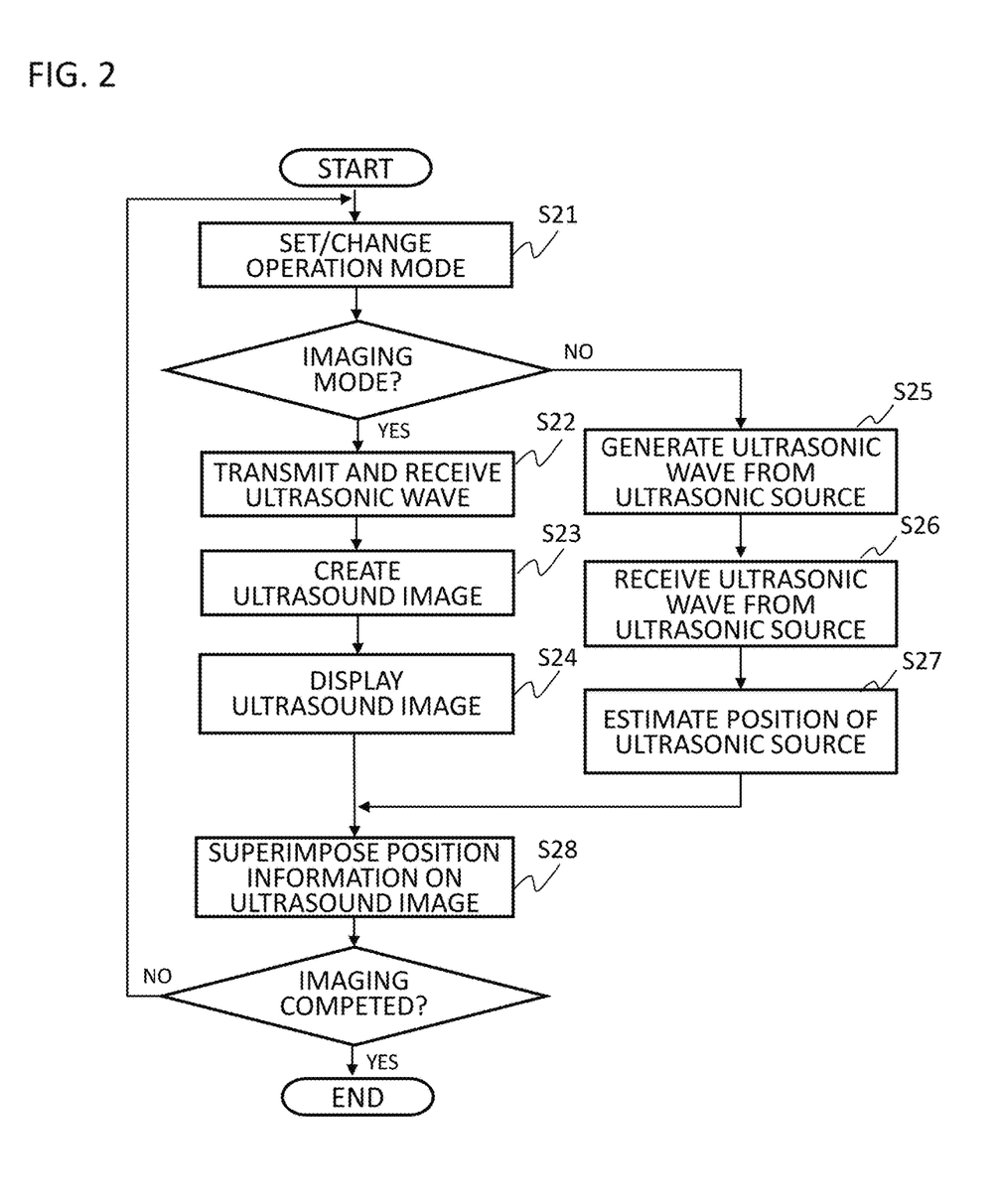
FIG. 2 is a flowchart showing an operation of the surgical operation support system according to an embodiment.

For executing the above-mentioned function, as shown in FIG. 2, the surgical operation support system 1 controls the ultrasound imaging apparatus 10 to operate in two operation modes (S21). One is an imaging mode for acquiring an ultrasound image of the subject, and the other is a device monitoring mode (hereinafter, simply referred to as a monitoring mode) for receiving a spontaneous ultrasonic wave from the ultrasonic source 20 to form an image. In the imaging mode, transmission and reception of ultrasonic waves to and from the imaging area are performed at imaging conditions being provided (S22) to create an ultrasound image such as a B-mode image (S23), and the ultrasound image is displayed on the display device 40 (S24). In the monitoring mode, the transmission in the imaging mode is deactivated (turned off) allowing the ultrasonic source 20 to generate ultrasonic waves (S25). The ultrasound imaging apparatus 10 continues reception of the ultrasonic waves being generated, and creates an image.

The position estimator 152 analyzes the GL artifacts appearing in the image created with the ultrasonic waves from the ultrasonic source 20 (S27), computes information such as position information and inclination, and displays a result of the analysis on the display device 40 (S28). The analysis result may be displayed in any mode on the display device 40, and it is not particularly limited. For example, the result may be shown in such a manner that a position relationship with respect to the imaging area can be identified, together with the ultrasound image displayed in step S23.

A control unit of the ultrasound imaging apparatus 10 may perform the switching between the imaging mode and the monitoring mode (S21), or the ultrasonic source 20 may transmit a trigger signal to the ultrasound imaging apparatus 10 to perform the switching according to this trigger signal. While the operator moves the device 2 in the body of the subject (in a blood vessel), the imaging mode and the monitoring mode of the ultrasound imaging apparatus 10 are alternately repeated, to display both the image of the imaging area including the affected part and the device position information on the display device 40, whereby the operator can identify how the device travels toward the imaging area.

In view of the outline of the surgical operation support system as described above, specific embodiments of the device position estimation will be described below. In the drawings referred to in the following embodiments, elements having the same functions are denoted by the same reference numerals, without redundant description.

Embodiment 1

An embodiment will be described in which a photoacoustic material is used as the ultrasonic source 20. FIG. 3 shows the overall configuration of the surgical operation support system 1 and the ultrasound imaging apparatus 10 according to the present embodiment.

The ultrasound imaging apparatus 10 has the same configuration as a general ultrasound imaging apparatus, except that a function is added for estimating the position of the ultrasonic source (position estimator 152). As shown in FIG. 3, the ultrasound imaging apparatus 10 includes a transmitter 11 for transmitting an ultrasonic signal to an ultrasound probe 3, a receiver 12 for receiving a reflected wave (RF signal) detected by the ultrasound probe 3 and performing processing such as phasing and summing, and a signal processor 150 for processing the RF signal received by the receiver 12. The ultrasound imaging apparatus 10 further includes a control unit 155 for controlling the entire apparatus and its accessory devices, an input device 13 for a user to input a condition and a command required for imaging, a display device 14 (FIG. 1: display device 40) for displaying an ultrasound image, a GUI (Graphic User Interface), and others acquired by the ultrasound imaging apparatus 10, and a memory 16 for storing an image and others which are processing results of the signal processor 150.

The signal processor 150 includes an ultrasound image former 151 that creates an ultrasound image using the signal received by the receiver 12, a position estimator 152 that estimates information regarding the position of the ultrasonic source 20 using the ultrasonic signal emitted from the ultrasonic source 20 and received by the receiver 12 through the ultrasound probe 3, and a display image former 153 that creates an image to be displayed on the display device 14. Here, among the ultrasonic signals received by the receiver 12, when it is necessary to distinguish between the ultrasonic signal being a reflected wave of the transmitted ultrasonic beam, and the ultrasonic signal from the ultrasonic source 20, the former is referred to as an image signal, the latter is referred to as a monitoring signal. The ultrasound image former 151 creates an image (referred to as a monitoring image) of the ultrasonic source 20 using the monitoring signal, in addition to the ultrasound image of the subject, such as a B-mode image. The position estimator 152 estimates a position and a direction (collectively referred to as position information) of the ultrasonic source 20 using the monitoring image.

A part or all of the functions of the units constituting the signal processor 150 and the control unit 155 may be implemented by uploading software having the functions programmed thereto to a computer including a CPU or a GPU, and a memory. In the example shown in FIG. 3, functions of the signal processor 150 and the control unit 155 are combined as a single processing unit 15. However, some or all of the functions of the respective portions may be implemented by electronic circuitry, hardware such as ASIC, FPGA, or the like. Some functions of the processing unit 15 may be implemented by a computer independent of the ultrasound imaging apparatus 10.

Various types of ultrasound probes are adoptable as the ultrasound probe 3, such as a 1D array probe in which a large number of transducer elements are arranged in a one-dimensional direction, a 1D3 array probe having an array arrangement of two or three rows in a direction perpendicular to the array direction of the 1D array probe, or a 2D array probe having a large number of array arrangements in a two-dimensional direction.

Figure 4:
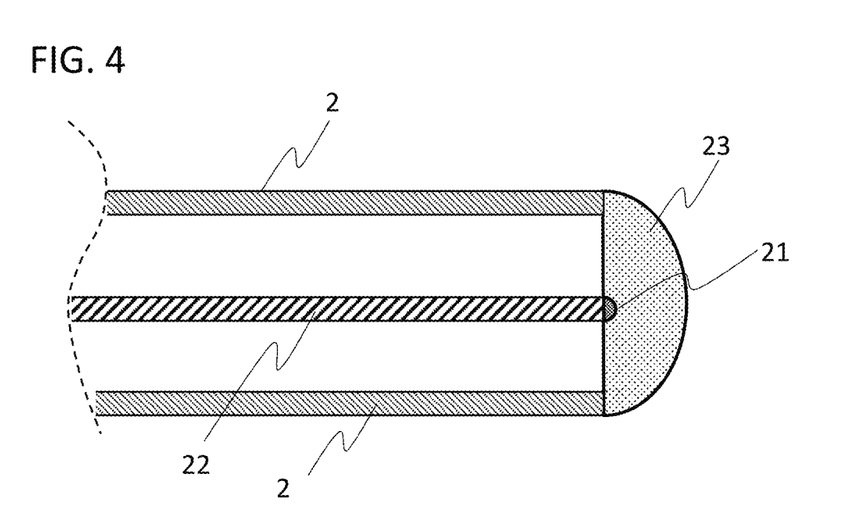
FIG. 4 is a sectional view showing a structure of a device tip.

The ultrasonic source 20 may comprise a material that adiabatically expands upon receipt of a laser beam and emits an ultrasonic wave such as a photoacoustic signal, for example, a publicly known dye (photosensitizer), metal nanoparticle, carbon-based compound, and others. As shown in FIG. 4, for example, the ultrasonic source 20 has a structure that the aforementioned photoacoustic material 21 is fixed to the insertion-side end surface of an optical fiber 22 disposed in a hollow portion of the flexible hollow device 2 (e.g., a guide wire), covered with a resin sealing member 23. A light generator for generating a laser beam (light generator) 25 is connected to the other end of the optical fiber 22 (opposite to the end portion to which the photoacoustic material 21 is fixed), and the photoacoustic material 21 is irradiated with the laser beam from the light generator 25 through the optical fiber 22, and the photoacoustic material 21 emits photoacoustic signals, i.e., ultrasonic waves.

The light generator 25 sends a trigger signal to the ultrasound imaging apparatus 10 simultaneously emitting a laser beam. Upon receipt of this trigger signal, the ultrasound imaging apparatus 10 (control unit 155) puts the operation of the transmitter 11 on standby for a predetermined time period, and performs the operation in the monitoring mode. The time period to perform the operation in the monitoring mode may be determined in advance, or may be set by the user via the input device 13. Also, rather than a fixed time, the time may be variable such as gradually shortened, for example, depending on the traveling state of the device.

Figure 5:
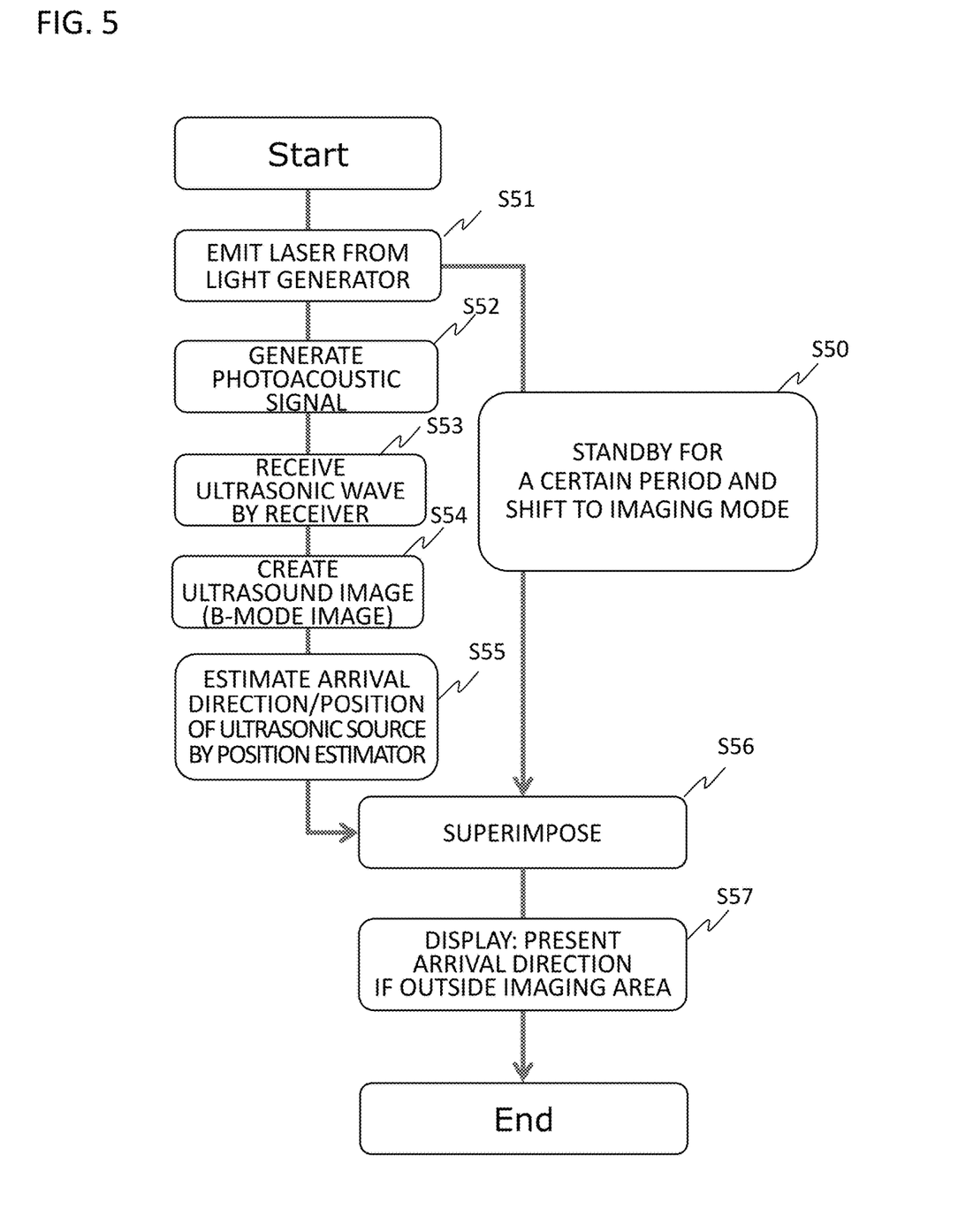
FIG. 5 illustrates an operation of the ultrasound imaging apparatus of Embodiment 1.

Next, with reference to the flowchart of FIG. 5, there will be described the operation of the surgical operation support system 1 having such configuration as described above. First, when imaging is started by setting the imaging area with respect to the affected part as an imaging target, the control unit 155 controls transmission and reception in the imaging mode, in the state where the trigger signal is not received from the light generator 25. That is, ultrasonic waves are transmitted and received to and from to the imaging area, and an ultrasound image of the imaging area is created.

Upon receiving the trigger signal from the light generator 25, the control unit 155 of the ultrasound imaging apparatus 10 switches the operation mode to the monitoring mode, putting the operation of the transmitter 11 on standby (S50). On the other hand, the light generator 25 generates a laser beam at a predetermined frequency, upon transmitting the trigger signal (S51). When the photoacoustic material is irradiated with the laser beam through the optical fiber and an ultrasonic wave is emitted from the ultrasonic source 20 (S52), the ultrasonic wave propagates in the subject as a spherical wave, and then detected by transducer elements of the ultrasound probe 3 (S53). The receiver 12 performs beamforming on the signal detected by each transducer element (phase addition), and passes to the ultrasound image former 151 as frame data. The ultrasound image former 151 forms an image (monitoring image) in the same manner as the creation of B-mode image in the imaging mode (S54), and passes the image to the position estimator 152.

Figure 6:
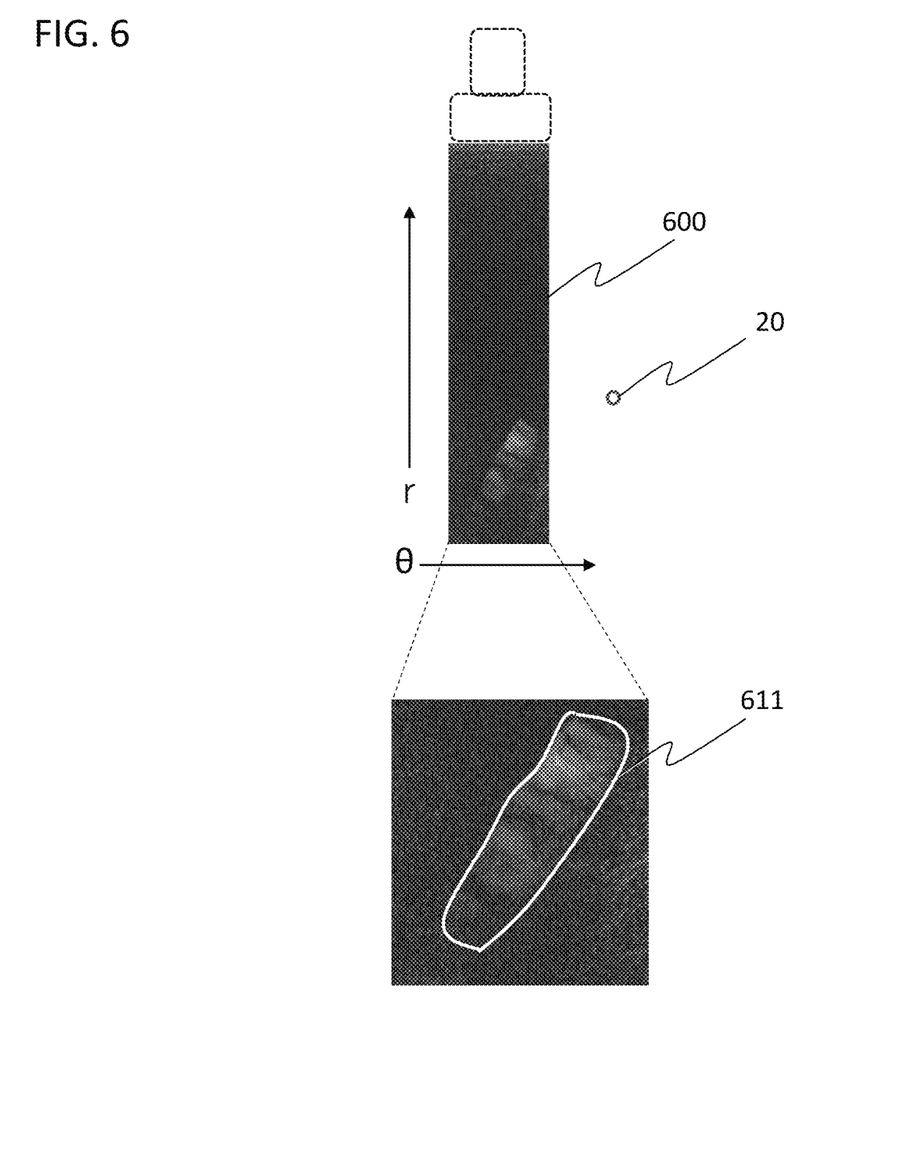
FIG. 6 illustrates GL artifacts.

The position estimator 152 estimates the position/direction of the ultrasonic source 20 based on the monitoring image received from the ultrasound image former 151 (S55). Here, when the ultrasonic source 20 is out of the imaging area determined by the condition of transmission and reception, the original image of the ultrasonic source 20 does not appear in the monitoring image. However, at a position where the angle of the ultrasonic wave reaching the transducer elements of the ultrasound probe 3 from the ultrasonic source is the same as the angle at which the grating lobe is generated, an artifact occurs in a similar manner as the grating lobe artifact. As a result, as shown in FIG. 6, a GL artifact 611 appears in the imaging area 600, for example. The lower view in FIG. 6 is an enlarged view of a part (artifact portion) of the upper view. Assuming the arrangement direction of the transducer elements as θ direction, and the depth direction as r direction, the GL artifact 611 represents that the side closer to the ultrasonic source 20 in the θ direction is high, as it becomes lower as going away therefrom, i.e., being skewed. This is because, as a result of the beamforming by the receiver 12, even at the same depth, those positioned closer are represented as positioned shallow, and those farther are represented as positioned deep. According to the slope of the monitoring image, it is possible to estimate which direction the ultrasonic source 20 is approaching, i.e., the arrival direction with respect to the imaging area.

Upon receipt of the monitoring image from the ultrasound image former 151, the position estimator 152 calculates the inclination of the artifact. If it is only required to know the arrival direction of the device, the inclination is not necessarily calculated as an exact angle. For example, the position estimator 152 extracts a region where the artifact occurs based on a brightness value of the image (a region with the brightness value higher or equal to a threshold value), and obtains the coordinates of both ends in the θ direction (depth), or the coordinates of both ends in the r direction (position in the θ direction), thereby determining the inclination of the region. Alternatively, an identifier to perform feature extraction by machine learning is employed, and the inclination may be obtained as a feature quantity, from the artifact image or from the region where the artifact image has been extracted.

Furthermore, a machine learning model such as CNN (convolutional Neural Network) may be used to estimate the arrival direction and the position. The machine learning model is a model having been trained by using a set of a large number of input data and training data, so as to output a correct solution in response to a new input. For example, B-mode images including various positions of the ultrasonic source are used to learn the relationship between the artifact and the position thereof. In this case, the position information may include not only the arrival direction, but also the distance from the imaging area and depth information.

In the example shown in FIG. 6, the GL artifact has appeared in the shape high on the right side and low on the left side, and the ultrasonic source 20 is estimated to arrive from the right side in the θ direction with respect to the imaging area 500.

After the arrival direction of the device 2 is estimated as described above, the position estimator 152 sends the result to the display image former 153.

Meanwhile, when a preset time has elapsed from the receipt of the trigger signal, the light generator 25 stops generating the laser beam, and the control unit 155 switches the operation mode to the imaging mode. The imaging mode is similar to normal imaging, and the subject is irradiated with the ultrasonic beam through the ultrasound probe 3, and the receiver 12 receives the image signal which is a reflected wave. The ultrasound image former 151 receives data corresponding to a plurality of frames from the receiver 12, creates the B-mode image, and sends the data to the display image former 153.

The display image former 153 uses information on the arrival direction of the device 2 received from the position estimator 152, and the ultrasound image received from the ultrasound image former 151, to create an image to be displayed on the display device 14 and then displays the image on the display device 14. There may be various modes in the way of displaying, but it is preferable to display the position information being superimposed on the screen showing the ultrasound image.

Figure 7A:
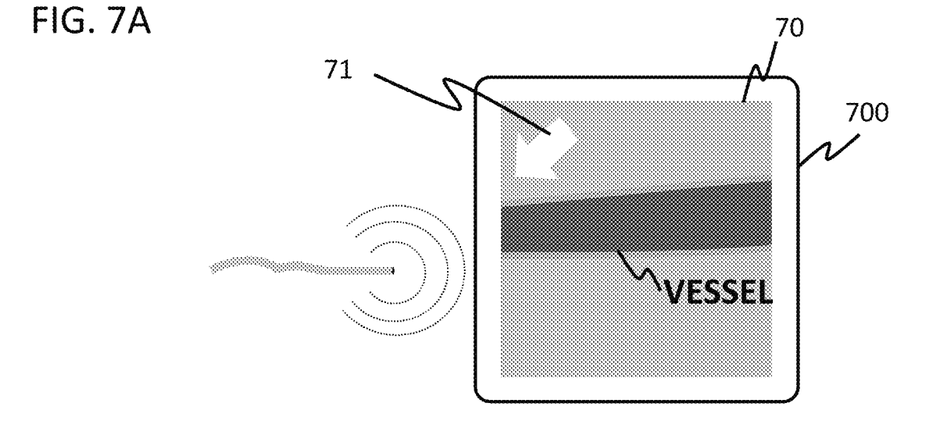
FIGS. 7A and 7B illustrate examples of a display screen of the ultrasound imaging apparatus of Embodiment 1.
Figure 7B:
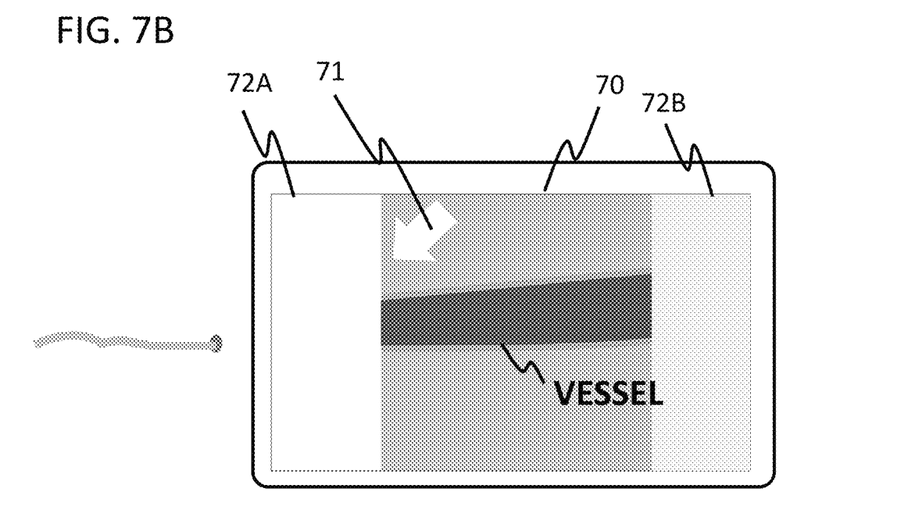

FIGS. 7A and 7B illustrate the display examples. In FIG. 7A, the arrow mark 71 indicating the arrival direction of the ultrasonic source 20, is superimposed on the screen 700 showing the imaging area 70. This allows the operator to recognize at a glance in which direction the device is moving through the vessel that is shown on the screen. FIG. 7B illustrates the screen showing the imaging area, provided with the regions 72A and 72B on both sides of the screen for indicating the direction. For example, when the device moves from the left side of the imaging area, the left region 72A is brightened to indicate the arrival direction. In this situation, the mark 71 shown in FIG. 7A may be displayed together. Further, though not shown, if not only the arrival direction but also the position of the ultrasonic source 20 is estimated, the position may be indicated by a mark such as a point in the regions 72A and 72B.

In the description above, the operation when the ultrasonic source 20 is outside the imaging area has been described. While the imaging mode and the monitoring mode are executed alternately, the ultrasonic source 20 is represented, for example, as a bright spot in the imaging area, when the device tip enters the imaging area. Therefore, it is possible to calculate the position of the ultrasonic source 20 based on the bright spot. A mark, or the like, indicating the device tip is displayed at a corresponding position in the ultrasound image acquired in the imaging mode, whereby it is possible to visually indicate the positional relationship between the vessel and the device as a target of the catheter treatment.

According to the present embodiment, even when the device tip is outside the imaging area, it is possible to estimate and present the arrival direction, according to the GL artifacts of the ultrasonic waves emitted from the ultrasonic source 20. This allows the operator to confirm on the ultrasound image, while the device is being inserted, from which direction the device tip is moving toward the affected area, and whether the device tip is reliably directed to the affected area.

Embodiment 2

Figure 8:
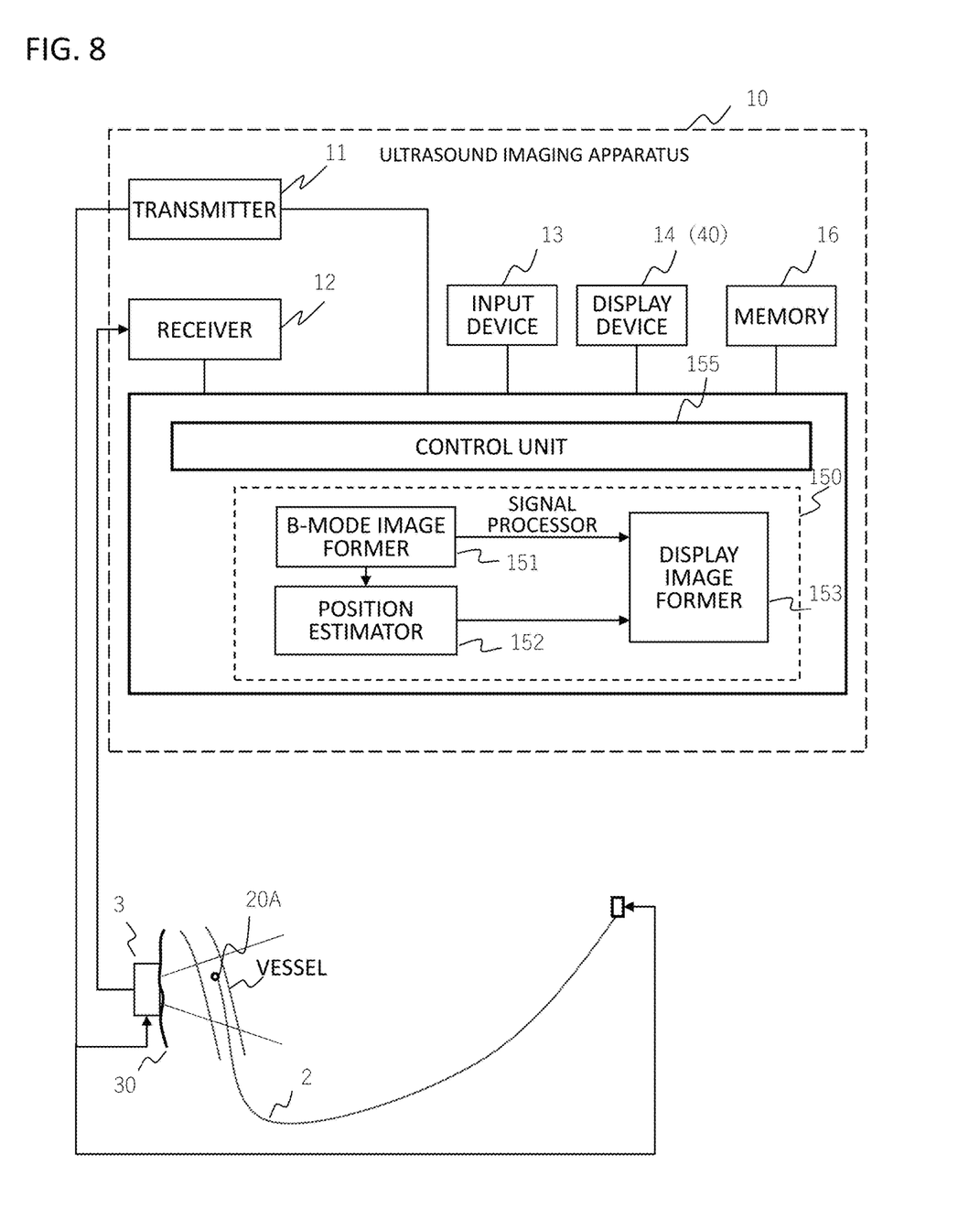
FIG. 8 illustrates an overall configuration of the ultrasound imaging apparatus of Embodiment 2.

In the present embodiment, a piezoelectric element is used as the ultrasonic source 20. The configuration of the ultrasound imaging apparatus 10 is the same as that of Embodiment 1. However, in the present embodiment, the light generator 25 for operating the ultrasonic source 20 is unnecessary, and the piezoelectric element is activated upon receipt of an electric signal from the transmitter 11 of the ultrasound imaging apparatus 10. There will now be described the present embodiment, focusing on the points different from Embodiment 1. FIG. 8 shows the configuration of the surgical operation support system of the present embodiment.

The piezoelectric element 20A vibrates when the electric signal (voltage) is applied in the same manner as the transducer of the ultrasound probe 3, and it is possible to generate the same ultrasonic wave as the ultrasonic wave generated by the ultrasound probe 3 by controlling the frequency of the signal. As the piezoelectric element 20A, a publicly known material such as piezoelectric ceramics can be used, which is fixed to the device tip. Also available is a catheter or a similar tool being a device having a tip equipped with the piezoelectric element as an actuator or a sensor, and this piezoelectric-element mounted device can be employed. The piezoelectric element 20A provided at the device tip is connected to a power source via a conductor passing through the catheter. A dedicated power supply may be used as the power source, but the example as shown in FIG. 8 has a configuration that the power source is connected to the transmitter 11 of the ultrasound imaging apparatus 10, whereby the piezoelectric element is driven by the signal from the transmitter 11.

Figure 9:
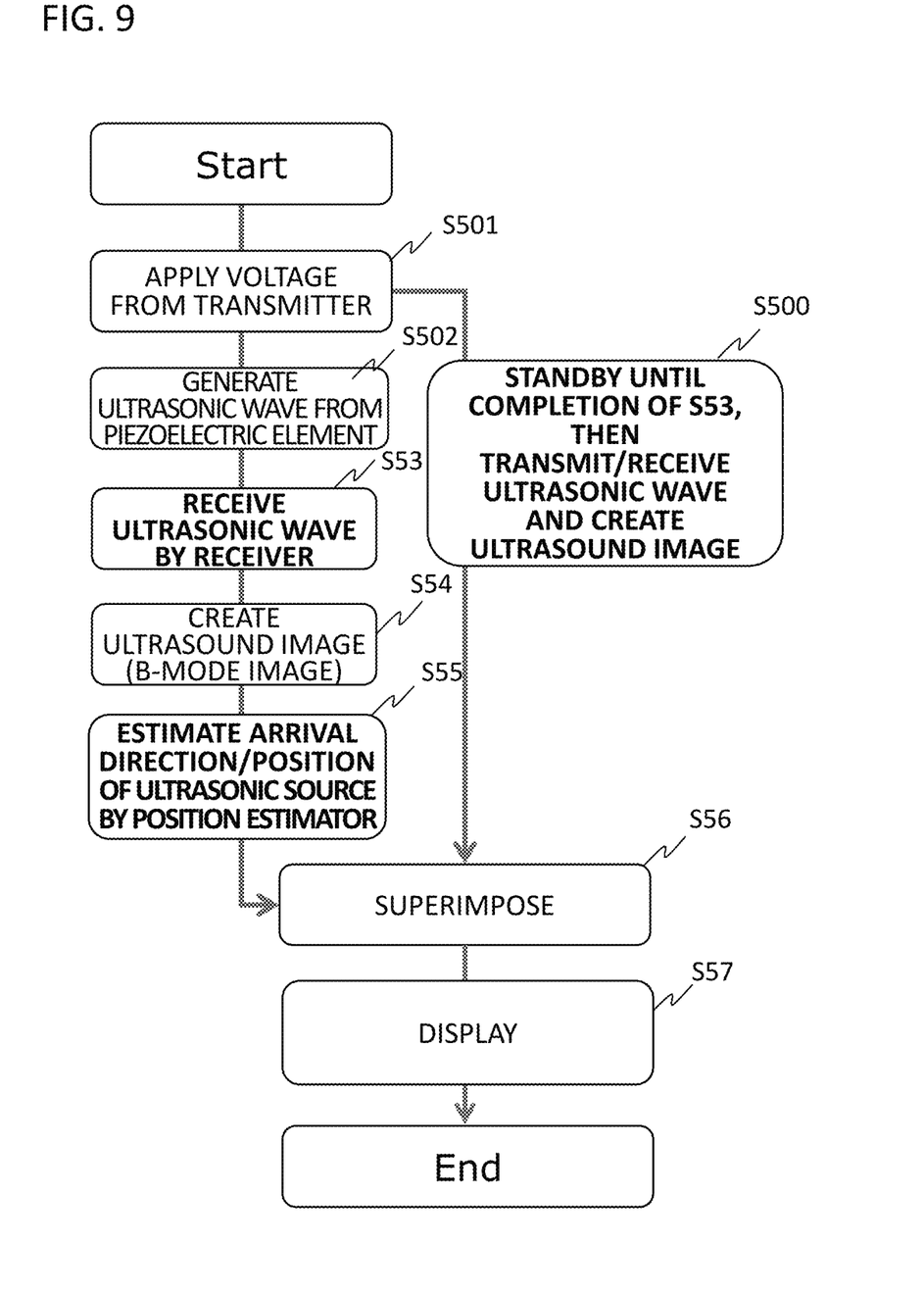
FIG. 9 illustrates an operation of the ultrasound imaging apparatus of Embodiment 2.

With reference to FIG. 9, the operation of the ultrasound imaging apparatus 10 having the configuration above will be described. There will now be described the case where the control unit 155 performs switching of the operation mode in the ultrasound imaging apparatus 10, for example. In FIG. 9, the same processes as in FIG. 5 are denoted by the same reference numerals, without redundant description.

In the monitoring mode, the control unit 155 operates the transmitter 11 to apply a pulse-like voltage to the piezoelectric element 20A, for example, at a predetermined repetition rate (S501). Then, a pulse-like ultrasonic wave is generated from the piezoelectric element 20A (S502). The ultrasonic wave generated from the piezoelectric element 20A shall correspond to the time for obtaining at least one frame worth of data. The ultrasonic wave from the piezoelectric element 20A is processed by the receiver 12 in the same manner as the ultrasonic wave received by the ultrasound probe 3, and a B-mode image is formed in the ultrasound image former 151 (S53, S54). The position estimator 152 estimates the position/direction of the piezoelectric element 20A using the B-mode image (S55). The method in which the position estimator 152 estimates the arrival direction of the piezoelectric element 20A is the same as that of Embodiment 1. Then, according to the angle of the GL artifacts appearing in the image, it is determined from which side of the imaging area the device 2 is approaching. When the piezoelectric element 20A enters the imaging area, the piezoelectric element 20A is represented, for example, as a bright spot in the B-mode image, and the position of the piezoelectric element on the image can be obtained.

Meanwhile, when the reception of the ultrasonic wave emitted from the piezoelectric element 20A is completed in the receiver 12, the control unit 155 switches the operation of the transmitter 11, sends a signal for driving the transducers of the ultrasound probe 3, and irradiates the subject with a beam-formed ultrasonic beam. The receiver 12 receives an RF signal, which is a reflected wave of the ultrasonic beam, adds beamforming thereto, and sends the RF signal to the ultrasound image former 151 (S50).

Thereafter, the display image former 153 superimposes the position information from the position estimator 152 (the arrival direction when outside the imaging area, and the position when inside the imaging area), on the ultrasound image formed by the ultrasound image former 151, so as to generate a display image and present the image on the display device 14 (S56, S57).

According to the present embodiment, similar to Embodiment 1, when the device 2 is outside the imaging area, the arrival direction is estimated, presenting it to the operator with high viewability. According to the present embodiment, by using the piezoelectric element as the ultrasonic source, it is possible to eliminate the need for the light generating device (light generator 25) to cause the emission from the photoacoustic material. In particular, the transmitter of the ultrasound imaging apparatus is configured to drive the piezoelectric element, thereby simplifying the system configuration.

Modification 1

In the above-described embodiments, the arrival direction and position of the ultrasonic source are estimated, and as shown in FIG. 7, when the ultrasonic source is outside the imaging area, the arrival direction is displayed in a visible manner. It is further possible to perform imaging, with changing a receiving condition so that the imaging area can include the ultrasonic source that has been outside the imaging area.

Figure 10:
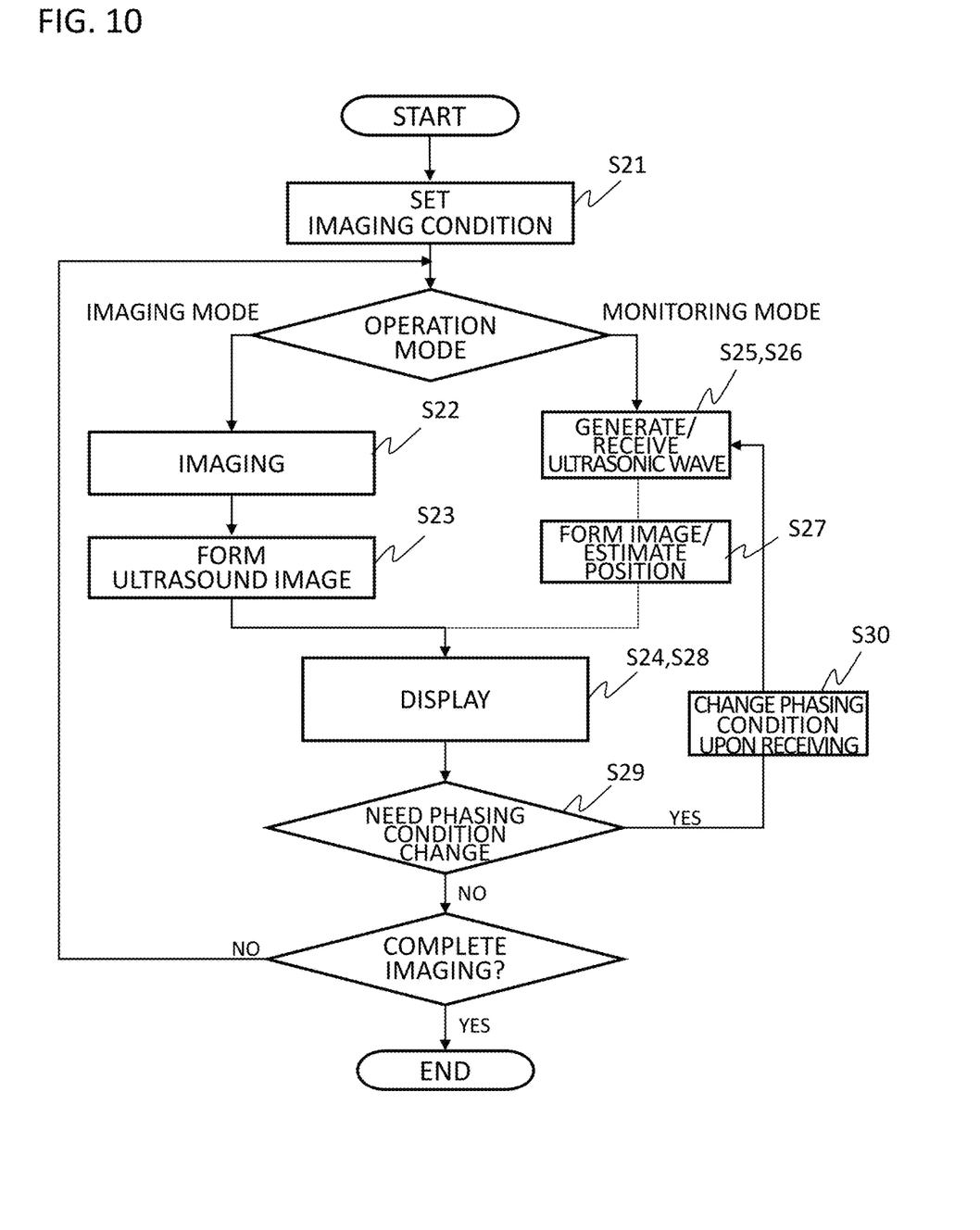
FIG. 10 illustrates an operation of Modification.

FIG. 10 is a flowchart showing a control example of the control unit when executing the present modification. In FIG. 10, the processing (S21 to S28) having the same descriptions as those of FIG. 2 are denoted by the same reference numerals, and redundant description thereof will be omitted. In the present modification, after the image of the position information superimposed on the ultrasound image is displayed in step S28, the control unit 155 determines whether to perform imaging for identifying the position of the ultrasonic source 20 (20A) (S29). If it is determined that the imaging is required, the phasing condition of the receiver 12 is changed so as to perform beamforming at the position of the estimated ultrasonic source 20 (S30), and then control is performed to activate the monitoring mode.

As for the determination in step S30, for example, after the superimposed images are displayed, when a user's instruction as a response to "whether or not the position identification of the ultrasonic source is necessary" is accepted via the input device 13, the determination may be performed according to the instruction, or the determination may be made based on the reliability of the artifact used for the estimation or of the estimated position information. For example, as described above, the GL artifacts have various inclinations depending on the position of the ultrasonic source, but the GL artifacts may also be changed when the depth of the ultrasonic source varies widely, or the like. In this case, the reliability of the position information estimated based on the inclination of the GL artifacts is low. It is also possible that the reliability is lowered because of unclear GL artifacts. If the CNN (Convolutional Neural Network) is used for the position estimation, for example, this reliability is delivered together with a confidence level of the outputted position information. Therefore, a degree of the reliability can be obtained by adopting this confidence level. The reliability may also be calculated from a brightness value of the GL artifacts, a distribution thereof, or other similar information. For example, if the brightness value (a maximum value or a summed value) does not satisfy a predetermined threshold, it is determined that the reliability is low.

Figure 11:
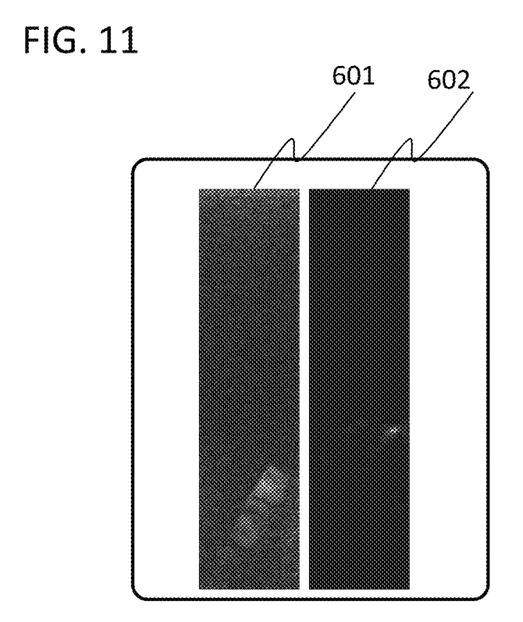
FIG. 11 shows a display example of Modification.

The display image former 153 displays the image obtained after changing the phasing condition in step S30 on the display device 14. As FIG. 11, for example, the image 601 used for the position estimation and the image 602 obtained by performing phasing at the estimated position may be placed side by side, or the ultrasound image of the imaging area may be displayed together. It is also possible that the processes S29 and S30 are repeated several times until an image of the ultrasonic source 20 is obtained. According to this kind of display, the operator can identify the estimated position and the arrival direction.

As described above so far, according to the present invention, when performing the catheter treatment, the catheter traveling status, which is the most important information for the operator, can be presented to the operator with high viewability in real time. While there have been described embodiments of the configurations and the operations, of the ultrasound imaging apparatus and the surgical operation support system of the present invention, the present invention also encompasses that an element described in the embodiments may be replaced with another element having the same function, and a different element may be added.

What is claimed is:

1. An ultrasound imaging apparatus, comprising:
a transmitter configured to transmit to a subject, an ultrasonic signal being beamformed through an ultrasound probe;
a receiver configured to beamform and receive a reflected ultrasonic wave from an imaging area irradiated with the ultrasonic signal; and
a computer, the computer programmed to:
create an ultrasound image of the imaging area from an ultrasonic wave, the ultrasonic wave being emitted from an ultrasonic source inserted into the subject and detected by the receiver in a monitoring mode to estimate a position information of the ultrasonic source, wherein the ultrasonic signal is not transmitted from the transmitter during the monitoring mode,
analyze an artifact of the ultrasound image within the imaging area to determine a shape and a slope of the artifact, the artifact being generated by the ultrasonic wave emitted from the ultrasonic source, the ultrasonic source being outside of the imaging area,
estimate the position information of the ultrasonic source with respect to the imaging area based on the shape and slope of the artifact,
wherein the ultrasonic source includes a light generator configured to transmit a trigger signal to the ultrasound imaging apparatus, and
wherein the computer is programmed to:
receive the trigger signal from the light generator,
in response to receiving the trigger signal, switch to an imaging mode from the monitoring mode, the imaging mode including the transmission of the ultrasonic signal via the transmitter and the reception of the reflected ultrasonic waves via the receiver from the imaging area,
wherein the imaging mode and the monitoring mode are alternately repeated according to the trigger signal,
wherein the ultrasonic source comprises a piezoelectric element that generates an ultrasonic wave when voltage is applied, and
wherein the transmitter transmits an electric signal to the piezoelectric element during the time when the ultrasonic signal is not transmitted.

2. The ultrasound imaging apparatus according to claim 1, wherein the position information includes any of a depth of the ultrasonic source, a distance up to the imaging area, and an arrival direction toward the imaging area.

3. The ultrasound imaging apparatus according to claim 1, wherein the computer is programmed to analyze an inclination of the artifact to estimate an arrival direction of the ultrasonic source by using the inclination of the artifact.

4. The ultrasound imaging apparatus according to claim 1, wherein the computer is programmed to execute an identifier that has learned a relationship between the artifact and the position information of the ultrasonic source.

5. The ultrasound imaging apparatus according to claim 1, further comprising,
a control unit configured to use position information of the ultrasonic source estimated by the computer, to perform control on a phase of beamforming by the receiver, so that the beamforming is performed on the position information being estimated.

6. The ultrasound imaging apparatus according to claim 5, wherein the computer is programmed to use the ultrasonic signal received by the receiver after the control on a phase of beamforming by the control unit, to estimate the position information of the ultrasonic source again.

7. The ultrasound imaging apparatus according to claim 5, wherein the computer is programmed to use an ultrasonic signal received by the receiver after the control on a phase of beamforming by the control unit, to create an image of the ultrasonic source, and display the image superimposed on a display displayed on a display device.

8. The ultrasound imaging apparatus according to claim 1, further comprising,
a display image former configured to form a display image representing the position information of the ultrasonic source, the position information being estimated by the computer.

9. The ultrasound imaging apparatus according to claim 8, wherein the computer is programmed to form the display image including the ultrasonic image of the image area and the position information on the same screen.

* * * * *